United States Patent
Ohno et al.

(10) Patent No.: US 8,114,814 B2
(45) Date of Patent: Feb. 14, 2012

(54) HERBICIDE COMPOSITION

(75) Inventors: Shuji Ohno, Tokyo (JP); Makoto Fujinami, Tokyo (JP); Yoshihiro Yamaji, Westchester, NY (US); Ryo Hanai, Tokyo (JP); Toshihiro Ikeuchi, Tokyo (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 12/529,031

(22) PCT Filed: Mar. 10, 2008

(86) PCT No.: PCT/JP2008/000505
§ 371 (c)(1),
(2), (4) Date: Aug. 28, 2009

(87) PCT Pub. No.: WO2008/114493
PCT Pub. Date: Sep. 25, 2008

(65) Prior Publication Data
US 2010/0069247 A1    Mar. 18, 2010

(30) Foreign Application Priority Data

Mar. 16, 2007  (JP) ................................ 2007-067874

(51) Int. Cl.
*A01N 43/02*    (2006.01)
*A01N 43/10*    (2006.01)

(52) U.S. Cl. ...................... 504/156; 504/116.1; 504/134

(58) Field of Classification Search ................... 504/134, 504/156, 116.1
See application file for complete search history.

(56) References Cited

U.S. PATENT DOCUMENTS

| 6,841,519 B1 | 1/2005 | Nakatani et al. ............... 504/271 |
| 7,238,689 B2 * | 7/2007 | Nakatani et al. ............ 514/227.8 |
| 2008/0013939 A1 | 6/2008 | Plant et al. ..................... 504/103 |

FOREIGN PATENT DOCUMENTS

| JP | 2004-002324 | 1/2004 |
| JP | 2005-145958 | 6/2005 |
| WO | WO 2006024820 A1 * | 3/2006 |

OTHER PUBLICATIONS

"Analogue." Merriam-Webster Online Dictionary. 2010. Merriam-Webster Online. Jun. 4, 2010 <http://www.merriam-webster.com/dictionary/analogue>.*

* cited by examiner

*Primary Examiner* — Anoop Singh
*Assistant Examiner* — Courtney Brown
(74) *Attorney, Agent, or Firm* — Bacon & Thomas, PLLC

(57) ABSTRACT

A herbicide composition contains, as a component A, one or more compounds selected from the group consisting of specific isoxazoline derivatives represented by the general formula [I] (wherein $R^1$ to $R^4$ represent each a hydrogen atom, an alkyl group, etc.; and Q represents $-S(O)n-(CR^5R^6)m-$, wherein n is an integer of 0 to 2, m is an integer of 1 to 3, and $R^5$ and $R^6$ represents each an alkyl group, etc.) and salts thereof; and, as a component B, a cyclohexanedione type compound, a phenylpyrazoline type compound or a sulfonyl aminocarbonyl triazine type compound and the like; as the active ingredients.

13 Claims, No Drawings

HERBICIDE COMPOSITION

TECHNICAL FIELD

The present invention relates to a novel herbicide composition.

BACKGROUND ART

Compounds represented by the later-shown formula [I] which are each the "component A" of the herbicide composition of the present invention, are known compounds described in Patent Literature 1, Patent Literature 4 and Patent Literature 5, which are safe to rice, wheat, barley, corn, grain sorghum, soybean, cotton, sugar beet, turf grass, fruit trees, etc. and which have excellent herbicidal effects by themselves.

Later-shown compounds which are each the "component B" or the "component C" used in the herbicide composition of the present invention, are known compounds having herbicidal activities and are described in, for example, Non-Patent Literatures 1 to 3.

Later-shown compounds described as "component D" are compounds each known as a safener and are described in Non-Patent Literatures 1 and 2.

In the Patent Literature 2 and the Patent Literature 3 are described application examples in which a compound represented by the formula [I] can be mixed with known herbicide compounds.

Patent Literature 1: WO 01/012613
Patent Literature 2: JP-A-2005-145958
Patent Literature 3: JP-A-2004-002324
Patent Literature 4: JP-A-2005-145958
Patent Literature 5: WO 2006/024820
Non-Patent Literature 1: Pesticide Manual 13th edition, British Crop Council
Non-Patent Literature 2: SHIBUYA INDEX 12th Edition, Publisher: SHIBUYA INDEX Research Group
Non-Patent Literature 3: Monthly Fine Chemical Vol. 35, No. 7 (2006) (CMC Publication)

DISCLOSURE OF THE INVENTION

1. Task to be Achieved by the Invention

The present invention aims at providing a herbicide composition containing an isoxazoline derivative represented by the later-shown formula [I] or a salt thereof, in order to control weeds which are undesirable in the cultivation of useful crops or useful plants.

2. Means for Achieving the Task

The present inventors made a study in order to achieve the above aim. As a result, the present inventors found that when the "component A" which is an isoxazoline derivative represented by the later-shown formula [I] or a salt thereof, is mixed with a herbicide shown in the later-shown "component B", or with the "component B" and a herbicide shown in the later-shown "component C", or with the "component B" and a safener shown in the later-shown "component D", or with the "component B", the "component C" and the "component D", the herbicidal effect obtained is not only the simple sum of the herbicidal effects of the individual components but also the synergism of the herbicidal effects of the individual components, or a lower phytotoxicity appears owing to the synergism.

That is, the present inventors found that, when two or more kinds of pesticides are used, as compared with the herbicidal range when each one of the pesticides is used independently, the herbicidal spectrum becomes wider, at the same time the herbicidal effect is achieved earlier; the effect lasts longer, and a sufficient effect is obtained at a smaller total dosage as compared with the same when each one of the pesticides is used independently; and that the safety to rice, wheat, barley, corn, grain sorghum, soybean, cotton, sugar beet, turf, fruit trees, etc. is secured and a sufficient herbicidal effect is obtained by one-time treatment. The finding has led to the completion of the present invention.

The present invention is characterized by having the following gist.

(1) A herbicide composition characterized by containing, as active ingredients, a component A which is at least one kind of compound selected from the group consisting of isoxazoline derivatives represented by the formula [I] described below and salts thereof, and a component B described below.

[Component A]:

[Formula 1]

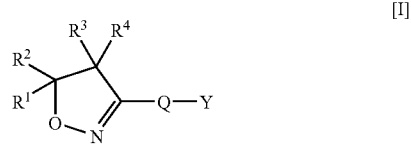

{In the formula, Q is a group —S(O)$_n$—(CR$^5$R$^6$)$_m$—; n is an integer of 0 to 2; m is an integer of 1 to 3;
R$^5$ and R$^6$ are each independently a hydrogen atom, a cyano group, an alkoxycarbonyl group, or a C1 to C6 alkyl group;
R$^1$ and R$^2$ are a hydrogen atom, a C1 to C8 alkyl group [which may be substituted with C3 to C8 cycloalkyl group, C1 to C6 alkoxy group, C1 to C6 alkylcarbonyl group, C1 to C6 alkylthio group, C1 to C6 alkylsulfinyl group, C1 to C6 alkylsulfonyl group, C1 to C6 alkylamino group, di(C1 to C6 alkyl)amino group, cyano group, C1 to C6 alkoxycarbonyl group, C1 to C6 alkylaminocarbonyl group, di(C1 to C6 alkyl)aminocarbonyl group, (C1 to C6 alkylthio)carbonyl group, carboxyl group, benzyloxy group (which may be substituted), phenoxy group (which may be substituted) or phenyl group (which may be substituted)], a C3 to C8 cycloalkyl group, a C1 to C6 alkoxycarbonyl group, a C1 to C6 alkylaminocarbonyl group, a di(C1 to C6 alkyl)aminocarbonyl group, a C1 to C8 alkylthiocarbonyl group, a carboxyl group, or a phenyl group (which may be substituted); or, R$^1$ and R$^2$ may form a C3 to C7 Spiro ring together with the carbon atom to which they bond;
R$^3$ and R$^4$ are a hydrogen atom, a C1 to C8 alkyl group which may be substituted with same or different, 1 to 3 halogen atoms, C3 to C8 cycloalkyl group or C1 to C6 alkoxy group, or a C3 to C8 cycloalkyl group; R$_3$ and R$_4$ may form a C3 to C7 spiro ring together with the carbon atom to which they bond;
or, either of R$^1$ and R$^2$ and either of R$^3$ and R$^4$ may form a 5- to 8-membered ring together with the carbon atoms to which they bond;
Y is a hydrogen atom, a C1 to C6 alkoxycarbonyl group, a carboxyl group, a C2 to C6 alkenyl group, a C1 to C10 alkyl group [which may be substituted with same or different, 1 to 3 halogen atoms, C1 to C6 alkoxy group, C2 to C8 alkenyloxy group, C2 to C8 alkinyloxy group, benzyloxy group (which may be substituted), C1 to C6 alkoxycarbonyl group, carboxyl group, hydroxyl group or formyl group], a phenyl group (substituted with same or different, 1 to 5 $R^7$s), or a naphthyl group (substituted with same or different, 1 to 5 $R^7$s;

$R^7$ is a hydrogen atom, a C1 to C6 alkyl group [which may be substituted with same or different, 1 to 3 halogen atoms, C1 to C6 alkoxy group, hydroxyl group, C1 to C6 alkylthio group, C1 to C6 alkylsulfinyl group, C1 to C6 alkylsulfonyl group, C1 to C6 alkylamino group, di (C1 to C6 alkyl) amino group, cyano group or phenoxy group (which may be substituted), a C1 to C6 alkoxy group (which may be substituted with same or different, 1 to 3 halogen atoms, C1 to C6 alkoxy group, 02 to CS alkenyl group, C2 to C6 alkinyl group, C2 to C6 alkenyloxy group, C2 to C6 alkinyloxy group, C1 to C6 alkoxycarbonyl group, C1 to C6 alkylcarbonyl group or C3 to C8 cycloalkyl group), a C3 to C8 cycloalkyloxy group, a C1 to C6 alkylthio group (which may be substituted with same or different, 1 to 3 halogen atoms or C1 to C6 alkoxy group), a C1 to C6 alkylsulfinyl group (which may be substituted with same or different, 1 to 3 halogen atoms or Cl to CS alkoxy group), a C1 to C6 alkylsulfonyl group (which may be substituted with same or different, 1 to 3 halogen atoms or C1 to C6 alkoxy group), a benzyloxy group (which may be substituted), an amino group [which may be substituted with C1 to C6 alkyl group, C1 to C6 alkylsulfonyl group, C1 to C6 alkylcarbonyl(C1 to C6 alkyl) group or C1 to C6 alkylsulfonyl(C1 to C6 alkyl) group], a halogen atom, a cyano group, a nitro group, a C1 to C6 alkoxycarbonyl group, a C3 to C8 cycloalkyloxycarbonyl group, a carboxyl group, a C2 to C6 alkenyloxycarbonyl group, a C2 to 6 alkinyloxycarbonyl group, a benzyloxycarbonyl group (which may be substituted), a phenoxycarbonyl group (which may be substituted), or a C1 to C6 alkylcarbnyloxy group.] and salts thereof.

Component B
At least one kind of compound selected from the group consisting of:
(B-1) Acetyl CoA carboxylase inhibition herbicides
  (a) Cyclohexanedione type compounds
    alloxydim, butroxydim, clethodim, cycloxydim, profoxydim, sethoxydim, tepraloxydim, tralkoxydim
  (b) Phenylpyrazoline type compounds
    aminopyralid
(B-2) Branched chain amino acid synthesis inhibitors
  (a) Sulfonylaminocarbonyltriazolinone type compounds
    flucarbazone-sodium
(B-3) Photosynthesis II inhibitors
  (a) Triazolinone type compounds
    amicarbazone
  (b) Uracil type compounds
    bromacil, lenacil, terbacil
  (c) Pyridazinone type compounds
    chloridazon
  (d) Phenyl carbamate type compounds
    desmedipham, phenmedipham
  (e) Urea type compounds
    chlorobromuron, chlorotoluron, chloroxuron, dimefuron, diuron, ethidimuron, fenuron, isoproturon, isouron, linuron, methabenzthiazuron, metobromuron, metoxuron, monolinuron, neburon, siduron, tebuthiuron
  (f) Hydroxybenzonitrile type compounds
    bromoxynil, ioxynil, bromofenoxim
  (g) Phenylpyridazine type compounds
    pyridate, pyridafol
(B-4) Photosynthesis I inhibitors
  (a) Bipyridium type compounds
    diquat, paraquat
(B-5) Protoporphyrin synthesis inhibitors
  (a) Phenylphthalimide type compounds
    cinidon-ethyl, flumiclorac-pentyl, flumioxazin
  (b) Thiadiazole type compounds
    fluthiacet-methyl, thidiazimin
  (c) pyrimidinedione type compounds
    butafenacil, benzfendizone
  (d) Phenylpyrazole type compounds
    pyraflufen-ethyl, fluazolate
  (e) Other compounds
    profluazol, flufenpyr-ethyl
(B-6) 4-Hydroxyphenylpyruvate dioxygenase inhibitors, carotenoid synthesis inhibitors
  (a) Pyridazinone type compounds
    norflurazon
  (b) Triazole type compounds
    amitrole
  (c) Isoxazolidinone type compounds
    clomazone
  (d) Pyridinecarboxamide type compounds
    diflufenican, picolinafen
  (e) Diphenyl ether type compounds
    aclonifen
  (f) Urea type compounds
    fluometuron
  (g) Other compounds
    beflubutamid, fluridone, fluorochloridone, flurtamone
(B-7) Folic acid synthesis inhibitors
  (a) Carbamate type compounds
    asulam
(B-8) Cell division inhibitors, very long-chain fatty acid synthesis inhibitors
  (a) Dinitroaniline type compounds
    benfluralin, butralin, dinitramine, ethalfluralin, oryzalin, pendimethalin, trifluralin
  (b) Benzenedicarboxylic acid type compounds
    chlorthal-dimethyl
  (c) Benzamide type compounds
    propyzamide, tebutam
  (d) Carbamate type compounds
    carbetamide, chlorpropham, propham
  (e) Other compounds
    piperophos
(B-9) Cellulose synthesis inhibitors
  (a) Benzonitrile type compounds
    dichlobenil, chlorthiamid
  (b) Benzamide type compounds
    isoxaben
  (c) Triazolocarboxamide type compounds
    flupoxame
(B-10) Cell membrane destroyers
  (a) Dinitrophenol type compounds
    dinoterb, DNOC
(B-11) Fatty acid synthesis inhibitors
  (a) Chlorocarboxylic acid type compounds
    TCA, dalapon, flupropanate
  (b) Phosphorodithioate type compounds
    bensulide
(B-12) Auxin synthesis inhibitors
  (a) Pyridinecarboxylic acid type compounds
    clopyralid, fluoroxypyr, picloram, triclopyr
  (b) Benzothiazolone type compounds
    benazolin (B-13) Auxin transfer inhibitors
  (a) Semicarbazone type compounds
    diflufenzopyr
  (b) Phthalate type compounds
    naptalam
(B-14) Others
  difenzoquat, flamprop-M, cinmethylin, fosamine, cumyluron, daimuron, methyl-daimuron, HC-252, forchlorfenuron, thidiazuron, pyrasulfotole, maleic hydrazide, diflumetorim, ancymidol, flurprimidol, chlormequat chloride, mepiquat chloride, quinmerac, propoxycarbazone-sodium, propoxycarbazone, flucetosulfuron, karbutilate, metobenzuron, prodiamine, triaziflam, pinoxaden, bencarbazone, topramezone, tembotrione, salts thereof and analogues thereof.

(2) A herbicide composition characterized by containing, as active ingredients, a herbicide composition set forth in the above (1) and a component C described below.

Component C
At least one kind of compound selected from the group consisting of:

(C-1) Acetyl CoA carboxylase inhibition herbicides
  (a) Aryloxyphenoxypropionic acid type compounds
    clodinafop-propargyl, cyhalofop-butyl, diclofop-methyl, fenoxaprop-P-ethyl, fenoxaprop-ethyl, fluazifop-butyl, fluazifop-P-butyl, haloxyfop, haloxyfop-P, haloxyfop-P-methyl, metamifop, propaquizafop, quizalofop-ethyl, quizalofop-P, quizalofop-P-ethyl, quizalofop-P-tefuryl
(C-2) Branched chain amino acid synthesis inhibitors
  (a) Sulfonylurea type compounds
    amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron-methyl-sodium, foramsulfuron, halosulfuron-methyl, imazosulfuron, iodosulfulon-methyl-sodium, mesosulfuron-methyl, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, trifloxysulfuron-sodium, triflusulfuron-methyl, tritosulfuron
  (b) Imidazolinone type compounds
    imazamethabenz-methyl, imazamox, imazapic, imazapyr, imazaquin, imazethapyr
  (c) Triazolopyrimidine type compounds
    cloransulam-methyl, diclosulam, florasulam, flumetsulam, metosulam, penoxsulam
  (d) Pyrimidinyloxy(thio)benzoic acid type compounds
    bispyribac-sodium, pyribenzoxim, pyriftalid, pyriminobac-methyl, pyrithiobacsodium
(C-3) Photosynthesis II inhibitors
  (a) Triazine type compounds
    ametryn, atrazine, cyanazine, dimethametryn, desmetryne, prometon, prometryn, propazine, simazine, simetryn, terbumeton, terbuthylazine, terbutryn, trietazine
  (b) Triazinone type compounds
    hexazinone, metamitron, metribuzin
  (c) Anilide type compounds
    pentanochlor, propanil
  (d) Benzothiadiazinon type compounds
    bentazone
(C-4) Protoporphyrin synthesis inhibitors
  (a) Diphenyl ether type compounds
    acifluorfen, bifenox, chiomethoxyfen, fluoroglycofen-ethyl, fomesafen, lactofen, oxyfluorfen
  (b) Oxadiazole type compounds
    oxadiargyl, oxadiazon
  (c) Triazolinone type compounds
    azafenidin, carfentrazone-ethyl, sulfentrazone
  (d) Oxazolidinedione type compounds
    pentoxazone
  (e) Other compounds
    pyraclonil
(C-5) 4-Hydroxyphenylpyruvate dioxygenase inhibitors, carotenoid synthesis inhibitors
  (a) Triketone type compounds
    mesotrione, sulcotrione, tefuryltrion
  (b) Isoxazole type compounds
    isoxaflutole, isoxachlortole
  (c) Pyrazole type compounds
    benzofenap, pyrazolynate, pyrazoxyfen
  (d) Other compounds
    benzobicyclon
(C-6) 5-Enolpyruvylshikimate 3-phosphate synthase inhibitors
  (a) Glycine type compounds
    glyphosate, glyphosate-trimesium
(C-7) Glutamine synthesis inhibitors
  (a) Phosphinic acid type compounds
    bilanafos, glufosinate
(C-8) Cell division inhibitors, ultra-long chain fatty acid synthesis inhibitors
  (a) Pyridine type compounds
    dithiopyr, thiazopyr
  (b) Phosphoroamidate type compounds
    butamifos, amiprophos-methyl
  (c) Chloroacetamide type compounds
    acetochlor, alachlor, butachlor, dimethachlor, dimethenamid, metazachlor, metolachior, pethoxamid, pretilachlor, propachior, propisochlor, S-metolachlor, thenylchlor
  (d) Oxyacetamide type compounds
    flufenacet, mefenacet
  (e) Tetrazolinone type compounds
    fentrazamide
  (f) Alkaneamide type compounds
    diphenamid, naproanilide, napropamide
  (g) Other compounds
    anilofos, cafenstrole
(C-9) Fatty acid synthesis inhibitors
  (a) Thiocarbamate type compounds
    butylate, cycloate, dimepiperate, EPTC, esprocarb, molinate, orbencarb, pebulate, prosulfocarb, thiobencarb, tiocarbazil, triallate, vernolate
  (b) Benzofuran type compounds
    benfuresate, ethofumesate
(C-10) Auxin synthesis inhibitors
  (a) Phenoxycarboxylic acid type compounds
    clomeprop, 2,4-D, 2,4-DB, dichlorprop, dichlorprop-P, MCPA, MCPB, mecoprop, mecoprop-P, MCPA-thioethyl
  (b) Benzoic acid type compounds
    2,3,6-TBA, dicamba, chloramben
  (c) Quinolinecarboxylic acid type compounds
    quinclorac (C-11) Others
bromobutide, oxaziclomefone, etobenzanid, indanofan, pyributicarb, pyrimisulfan,
salts thereof and analogues thereof.

(3) A herbicide composition characterized by containing, as active ingredients, a herbicide composition set forth in the above (1) and a component D described below.

Component D

At least one kind of compound selected from the group consisting of cloquintocet-mexyl, fenchlorazole-ethyl, mefenpyr, mefenpyr-diethyl, isoxadifen, isoxadifen-ethyl, furilazole, benoxacor, dichlormid, MON4660, oxabetrinil, cyometrinil, fenclorim, cyprosulfamide, naphthalic anhydride, flurazole, salts thereof and analogues thereof.

(4) A herbicide composition characterized by containing, as active ingredients, a herbicide composition set forth in the above (2) and a component D.

(5) A herbicide composition according to the above (1), which contains the component A and the component B at a weight ratio of 1:0.001 to 1:200.

(6) A herbicide composition according to the above (2), which contains the component A, the component B and the component C at a weight ratio of 1:0.001:0.001 to 1:200:200.

(7) A herbicide composition according to the above (3), which contains the component A, the component B and the component D at a weight ratio of 1:0.001:0.001 to 1:200:100.

(8) A herbicide composition according to the above (4), which contains the component A, the component B, the component C and the component D at a weight ratio of 1:0.001:0.001:0.001 to 1:200:200:100.

(9) A herbicide composition containing a herbicide composition set forth in any of the above (1) to (8), in an amount showing a herbicidal activity, at least one kind of inactive liquid carrier and/or solid carrier and, as necessary, at least one kind of surfactant.

(10) A method for preparing a herbicide composition set forth in any of the above (1) to (9), which comprises mixing a component A and a component B and, as necessary, a component C and/or a component D, at least one kind of inactive liquid carrier and/or solid carrier, and a surfactant.

(11) A method for controlling undesired vegetation, which comprises applying the active ingredients contained in a herbicide composition set forth in any of the above (1) to (9), at one time or in portions before the budding of the undesired vegetation, and/or during the budding, and/or after the budding.

EFFECTS THE INVENTION

The herbicide composition of the present invention exhibits not only the simple sum of the herbicidal effects of the individual components but also the synergism of the herbicidal effects of the individual components, and also shows a lower phytotoxicity owing to the synergism; therefore, the present herbicidal composition can be applied at a reduced dosage. Further, the present herbicidal composition is highly safe to useful crops and can control various weeds which cause problems in paddy field, upland field, non-crop land, etc., over a long period from before budding to growing stage.

BEST MODE FOR CARRYING OUT THE INVENTION

The definitions of the terms used in the present DESCRIPTION are given below.

Halogen atom refers to fluorine atom, chlorine atom, bromine atom or iodine atom.

Alkyl group refers to straight chain or branched chain alkyl group having 1 to 10 carbon atoms, unless otherwise specified. There can be mentioned, for example, methyl group, ethyl group, n-propyl group, isopropyl group, n-butyl group, isobutyl group, sec-butyl group, tert-butyl group, n-pentyl group, isopentyl group, neopentyl group, n-hexyl group, isohexyl group, 3,3-dimethylbutyl group, heptyl group, octyl group or decyl group.

Cycloalkyl group refers to cycloalkyl group having 3 to 8 carbon atoms. There can be mentioned, for example, cyclopropyl group, cyclobutyl group, cyclopentyl group or cyclohexyl group.

Alkoxy group refers to (alkyl)-O— group wherein the alkyl moiety has the same definition as given above. There can be mentioned, for example, methoxy group or ethoxy group.

Alkylthio group, alkylsulfinyl group and alkylsulfonyl group refer to (alkyl)-S— group, (alkyl)-SO— group and (alkyl)-$SO_2$ group, wherein the alkyl moiety has the same definition as given above. There can be mentioned, for example, methylthio group, ethylthio group, methylsulfinyl group, methylsulfonyl group or ethylsulfonyl group.

Alkenyl group refers to straight chain or branched chain alkenyl group having 2 to 6 carbon atoms. There can be mentioned, for example, ethenyl group, 1-propenyl group, 2-propenyl group, isopropenyl group, 1-butenyl group, 2-butenyl group, 3-butenyl group or 2-pentenyl group.

Alkinyl group refers to straight chain or branched chain alkinyl group having 2 to 6 carbon atoms. There can be mentioned, for example, ethinyl group, 2-propinyl group, 2-butinyl group or 3-butinyl group.

Alkenyloxy group and alkinyloxy group refer to (alkenyl)-O— group and (alkinyl)-O— group, wherein the alkenyl or alkinyl moiety has the same definition as given above. There can be mentioned, for example, 2-propenyloxy group and 2-propinyloxy group.

Alkylamino group and dialkylamino group refer to (alkyl)-NH— group and (alkyl)$_2$N— group, wherein the alkyl moiety has the same definition as given above. There can be mentioned, for example, methylamino group, ethylamino group, dimethylamino group.

Alkylcarbonyl group, (alkylthio)carbonyl group, alkoxycarbonyl group, alkylaminocarbonyl group and dialkylaminocarbonyl group refer to (alkyl)-CO— group, (alkylthio)-CO— group, (alkoxy)-CO— group, (alkylamino)-CO— group and (dialkylamino)-CO— group, wherein the alkyl, alkylthio, alkoxy, alkylamino or dialkylamino moiety has the same definition as given above. There can be mentioned, for example, acetyl group, methylthiocarbonyl group, ethoxycarbonyl group, methoxycarbonyl group, methylaminocarbonyl group and dimethylaminocarbonyl group.

Alkylaminocarbonylamino group, dialkylaminocarbonylamino group and alkoxycarbonylamino group refer to (alkylaminocarbonyl)-NH— group, (dialkylaminocarbonyl)-NH— group and (alkoxycarbonyl)-NH— group, wherein the alkylaminocarbonyl, dialkylaminocarbonyl or alkoxycarbonyl moiety has the same definition as given above. There can be mentioned, for example, methylaminocarbonylamino group, dimethylaminocarbonylamino group and methoxycarbonylamino group.

As the phenyl group which may be substituted, there can be mentioned phenyl group having, on the phenyl ring, 1 to 5 substituents such as halogen atoms, C1 to C6 alkyl groups, C1 to C6 alkoxy groups and the like.

As the phenoxy group which may be substituted, there can be mentioned phenoxy group having, on the phenyl ring, 1 to 5 substituents such as halogen atoms, C1 to C6 alkyl groups, C1 to C6 alkoxy groups and the like.

As the benzyloxy group which may be substituted, there can be mentioned benzyloxy group having, on the phenyl ring and at the benzyl position, 1 to 7 substituents such as halogen atoms, C1 to C6 alkyl groups, C1 to C6 alkoxy groups and the like.

As the phenoxycarbonyl group which may be substituted, there can be mentioned phenoxycarbonyl group having, on the phenyl ring, 1 to 5 substituents such as halogen atoms, C1 to C6 alkyl groups, C1 to C6 alkoxy groups and the like.

In the present invention, the salts included in the component A, the component B, the component C and the component D include all agriculturally acceptable salts. There can be mentioned, for example, salts of alkali metals such as lithium, sodium, potassium and the like; salts of alkaline earth metals such as calcium, magnesium and the like; ammonium salts; salts of organic amines such as methylamine, triethylamine, diethanolamine, piperidine, pyridine and the like; salts of carboxylic acids such as acetic acid, propionic acid, oxalic acid, trifluoroacetic acid, benzoic acid and the like; salts of sulfonic acids such as methanesulfonic acid, trifluoromethanesulfonic acid, p-toluenesulfonic acid and the like; and salts of inorganic acids such as hydrochloric acid, sulfuric acid, nitric acid, carbonic acid and the like.

The analogues of the compounds included in the component B, the component C and the component D include ester derivatives or acyl derivatives of the functional groups present in the compounds described as the component B, the component C and the component D; and there can be mentioned, for example, acetic acid ester derivatives, formic acid ester derivatives and benzoic acid ester derivatives of alcohol; and acetyl derivatives and benzoyl derivatives of amine.

The compounds represented by the general formula [I] of the component A which is an active ingredient of the present invention composition, can be produced by the methods described in the Patent Literatures 1 to 4 or by methods based thereon, and specific examples and application examples of the compounds are described in these Patent Literatures.

Representative examples of the compounds are shown in Table 1 to Table 3.

Incidentally, in the present DESCRIPTION, for example, the following expressions in the tables represent the following groups.

Me: methyl group; Et: ethyl group;
Pr: n-propyl group; Pr-iso: isopropyl group;
OMe: methoxy group; OEt: ethoxy group;
OPr: propoxy group; OPr-iso: isopropoxy group;
Ph: phenyl group Also, for example, Ph(4-Cl) represents a 4-chlorophenyl group in which the 4-position of phenyl group is substituted with a chlorine atom; Ph(2,6-$F_2$) represents a 2,6-difluorophenyl group in which the 2- and 6-positions of phenyl group are substituted with fluorine atoms; and Ph(2-F, 3-Cl, 6-OCHF$_2$) represents a 3-chloro-2-fluoro-6-trifluoromethoxyphenyl group in which the 2-position of phenyl group is substituted with a fluorine atom, the 3-position of the phenyl group is substituted with a chlorine atom, and the 6-position of the phenyl group is substituted with a difluoromethyl group.

TABLE 1

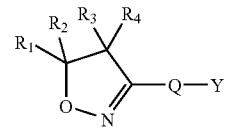

| Compound No. | $R_1$ | $R_2$ | $R_3$ | $R_4$ | Q | Y | Melting point (° C.) or Refractive index ($n_D^{20}$) |
|---|---|---|---|---|---|---|---|
| 1 | Me | Me | H | H | SCH$_2$ | Ph | 1.5521 |
| 2 | Et | Me | H | H | SOCH$_2$ | Ph(2,6-F$_2$) | 30° C. 以下 |
| 3 | Et | Me | H | H | SO$_2$CH$_2$ | Ph(2,6-F$_2$) | 64~65° C. |
| 4 | Me | Me | H | H | SO$_2$CH$_2$ | Ph(2,6-F$_2$) | 110~111° C. |
| 5 | Me | Me | H | H | SCH$_2$ | Ph(2,6-F$_2$) | 77~80° C. |
| 6 | Me | Me | H | H | SO$_2$CH$_2$ | H | 82~84° C. |
| 7 | Me | Me | H | H | SO$_2$CH$_2$ | Ph(2-CF$_3$, 5-Cl) | 72~73° C. |
| 8 | Me | Me | H | H | SO$_2$CH$_2$ | Ph(2-NO$_2$, 5-Cl) | 98~100° C. |
| 9 | Me | Me | H | H | SO$_2$CH$_2$ | Ph(2-CN, 5-Cl) | 173~174° C. |
| 10 | Me | Me | H | H | SO$_2$CH$_2$ | Ph(2-OMe, 5-Cl) | 113~114° C. |
| 11 | Me | Me | H | H | SO$_2$CH$_2$ | Ph(2-OEt, 5-Cl) | 120~122° C. |
| 12 | Me | Me | H | H | SO$_2$CH$_2$ | Ph(2-OCF$_2$H, 5-Cl) | 53~54° C. |
| 13 | Me | Me | H | H | SO$_2$CH$_2$ | Ph(2,5-Cl$_2$) | 123~124° C. |
| 14 | Me | Me | H | H | SO$_2$CH$_2$ | Ph(2-Me, 5-Cl) | 110~111° C. |
| 15 | Me | Me | H | H | SO$_2$CH$_2$ | Ph(2-COOMe, 5-Cl) | 98~100° C. |
| 16 | Me | Me | H | H | SO$_2$CH$_2$ | Ph(2-OCF$_2$H, 5-Me) | 71~73° C. |
| 17 | Me | Me | H | H | SO$_2$CH$_2$ | Ph(2-OCF$_2$H, 5-OMe) | 70~71° C. |
| 18 | Me | Me | H | H | SO$_2$CH$_2$ | Ph(2,3-(OCF$_2$H)$_2$) | 84~86° C. |
| 19 | Me | Me | H | H | SO$_2$CH$_2$ | Ph(2-OCF$_2$H, 4-Cl) | 80~82° C. |
| 20 | Me | Me | H | H | SO$_2$CH$_2$ | Ph(2-CN, 6-Cl) | 134~136° C. |
| 21 | Me | Me | H | H | SO$_2$CH$_2$ | Ph(2-OCF$_2$H, 6-Cl) | 83~84° C. |
| 22 | Me | Me | H | H | SO$_2$CH$_2$ | Ph(2-CN, 6-F) | 112~114° C. |
| 23 | Me | Me | H | H | SO$_2$CH$_2$ | Ph(2-NO$_2$, 6-F) | 146~147° C. |
| 24 | Me | Me | H | H | SO$_2$CH$_2$ | Ph(3-Cl, 4-OEt) | 110~111° C. |
| 25 | Me | Me | H | H | SO$_2$CH$_2$ | Ph(2,6-(OCF$_2$H)$_2$) | 65~66° C. |
| 26 | Me | Me | H | H | SO$_2$CH$_2$ | Ph(2,3,6-Cl$_3$) | 158~160° C. |

TABLE 2

| Compound No. | $R_1$ | $R_2$ | $R_3$ | $R_4$ | Q | Y | Melting point (° C.) or Refractive index ($n_D^{20}$) |
|---|---|---|---|---|---|---|---|
| 27 | Me | Me | H | H | SO$_2$CH$_2$ | Ph(2,3-Cl$_2$, 6-CF$_3$) | 91~93° C. |
| 28 | Me | Me | H | H | SO$_2$CH$_2$ | Ph(2,3-Cl$_2$, 6-OMe) | 166~168° C. |
| 29 | Me | Me | H | H | SO$_2$CH$_2$ | Ph(2,3-Cl$_2$, 6-OEt) | 99~100° C. |
| 30 | Me | Me | H | H | SO$_2$CH$_2$ | Ph(2,3-Cl$_2$, 6-OCF$_2$H) | 96~97° C. |
| 31 | Me | Me | H | H | SO$_2$CH$_2$ | Ph(2,3-Cl$_2$, 6-OCH$_2$CF$_3$) | 135~137° C. |
| 32 | Me | H | H | H | SO$_2$CH$_2$ | Ph(2,3-Cl$_2$, 6-OCH$_2$CF$_3$) | 84~86° C. |
| 33 | Me | Me | H | H | SO$_2$CH$_2$ | Ph(2,3-Cl$_2$, 6-OCH$_2$C≡CH) | 113~115° C. |
| 34 | Me | Me | H | H | SO$_2$CH$_2$ | Ph(2,3-Cl$_2$, 6-OCH$_2$CF$_2$H) | 118~120° C. |
| 35 | Me | Me | H | H | SO$_2$CH$_2$ | Ph(2,3-F$_2$, 6-OEt) | 75~76° C. |

TABLE 2-continued

| Compound No. | $R_1$ | $R_2$ | $R_3$ | $R_4$ | Q | Y | Melting point (° C.) or Refractive index ($n_D^{20}$) |
|---|---|---|---|---|---|---|---|
| 36 | Me | Me | H | H | $SO_2CH_2$ | Ph(2-F, 3-Cl, 6-OEt) | 95~96° C. |
| 37 | Me | Me | H | H | $SO_2CH_2$ | Ph(3,6-$Cl_2$, 2-OEt) | 103~105° C. |
| 38 | Me | Me | H | H | $SO_2CH_2$ | Ph(2-F, 3-Cl, 6-$OCF_2H$) | 64~65° C. |
| 39 | Me | Me | H | H | $SO_2CH_2$ | Ph(2-F, 3-Cl, 6-$CF_3$) | 83~84° C. |
| 40 | Me | Me | H | H | $SO_2CH_2$ | Ph(2,4,5-$Cl_3$) | 138~139° C. |
| 41 | Me | Me | H | H | $SO_2CH_2$ | Ph(4,5-$Cl_2$, 2-OEt) | 121~122° C. |
| 42 | Me | Me | H | H | $SO_2CH_2$ | Ph(5-Cl, 4-F, 2-OEt) | 136~138° C. |
| 43 | Me | Me | H | H | $SO_2CH_2$ | Ph(3,5-$Cl_2$, 2-OEt) | 60~61° C. |
| 44 | Me | Me | H | H | $SO_2CH_2$ | Ph(2,4-$Cl_2$, 6-OMe) | 131~132° C. |
| 45 | Me | Me | H | H | $SO_2CH_2$ | Ph(2,4-$Cl_2$, 6-OEt) | 98~99° C. |
| 46 | Me | Me | H | H | $SO_2CH_2$ | Ph(2,4-$Cl_2$, 6-OPr) | 81~82° C. |
| 47 | Me | Me | H | H | $SO_2CH_2$ | Ph(2,4-$Cl_2$, 6-OPr-iso) | 80~83° C. |
| 48 | Me | Me | H | H | $SO_2CH_2$ | Ph(2,4-$Cl_2$, 6-$OCH_2CF_3$) | 143~144° C. |
| 49 | Me | Me | H | H | $SO_2CH_2$ | Ph(2,4,6-$(OCF_2H)_2$) | 55-56° C. |
| 50 | Me | Me | H | H | $SO_2CH_2$ | Ph(2,5-$(Me)_2$, 4-OEt) | 125~126° C. |
| 51 | Me | Me | H | H | $SO_2CH_2$ | Ph(2,5-$Cl_2$, 4-OMe) | 126~127° C. |
| 52 | Me | Me | H | H | $SCH_2$ | Ph(2,5-Cl2, 4-OEt) | 62~63° C. |
| 53 | Me | Me | H | H | $SOCH_2$ | Ph(2,5-$Cl_2$, 4-OEt) | 115~117° C. |
| 54 | Me | Me | H | H | $SO_2CH_2$ | Ph(2,5-$Cl_2$, 4-OEt) | 155~156° C. |

TABLE 3

| Compound No. | $R_1$ | $R_2$ | $R_3$ | $R_4$ | Q | Y | Melting point (° C.) or Refractive index ($n_D^{20}$) |
|---|---|---|---|---|---|---|---|
| 55 | Me | H | H | H | $SO_2CH_2$ | Ph(2,5-$Cl_2$, 4-OEt) | 94~95° C. |
| 56 | Me | Me | H | H | $SO_2CH_2$ | Ph(2-Cl, 4-OEt, 5-Me) | 123~125° C. |
| 57 | Me | Me | H | H | $SO_2CH_2$ | Ph(2,5-$Cl_2$, 4-$OCF_2H$) | 106~107° C. |
| 58 | Me | Me | H | H | $SO_2CH_2$ | Ph(2,4-$(OEt)_2$, 5-Cl) | 139~140° C. |
| 59 | Me | Me | H | H | $SO_2CH_2$ | Ph(2-F, 4-OEt, 5-Cl) | 116~118° C. |
| 60 | Me | Me | H | H | $SO_2CH_2$ | Ph(2-$OCH_2CF_3$, 4-OEt, 5-Cl) | 115~116° C. |
| 61 | Me | Me | H | H | $SO_2CH_2$ | Ph(2-OEt, 4-OMe, 5-Cl) | 135~136° C. |
| 62 | Me | Me | H | H | $SO_2CH_2$ | Ph(2-$CF_3$, 4-OEt, 5-Cl) | 67~70° C. |
| 63 | Me | Me | H | H | $SO_2CH_2$ | Ph(2,5-$Cl_2$, 4-$NO_2$) | 141~142° C. |
| 64 | Me | Me | H | H | $SO_2CH_2$ | Ph(2,5-$(COOMe)_2$, 4-Me) | 128~129° C. |
| 65 | Me | Me | H | H | $SO_2CH_2$ | Ph(2-Cl, 4-$NO_2$, 5-OMe) | 156~157° C. |
| 66 | Me | Me | H | H | $SO_2CH_2$ | Ph(2-Cl, 4-$NO_2$, 5-OEt) | 153~154° C. |
| 67 | Me | Me | H | H | $SO_2CH_2$ | Ph(2,6-$(OEt)_2$, 3-$NO_2$) | 114~115° C. |
| 68 | Me | Me | H | H | $SO_2CH_2$ | Ph(2,6-$(OEt)_2$, 3-Cl) | 190~191° C. |
| 69 | Me | Me | H | H | $SO_2CH_2$ | Ph(2,6-$Cl_2$, 3-$OCH_2CF_3$) | 125~127° C. |
| 70 | Me | Me | H | H | $SO_2CH_2$ | Ph(2-OEt, 3,4-$Cl_2$) | 103~104° C. |
| 71 | Me | Me | H | H | $SO_2CH_2$ | Ph(2,3-$Cl_2$, 4-OEt) | 161~162° C. |
| 72 | Me | Me | H | H | SO2CH2 | Ph(3,5-$Cl_2$, 4-OEt) | 134~135° C. |
| 73 | Me | Me | H | H | $SO_2CH_2$ | Ph(2,5-$Cl_2$, 3,6-$(Me)_2$) | 119~121° C. |
| 74 | Me | Me | H | H | $SO_2CH_2$ | Ph(2,5-$(OEt)_2$, 3,6-$(Me)_2$) | 72~73° C. |
| 75 | Me | Me | H | H | $SO_2CH_2$ | Ph(2-OEt, 3,5,6-$Cl_3$) | 104~106° C. |
| 76 | Me | Me | H | H | $SO_2CH_2$ | Ph(2,3,4-$F_3$, 6-$OCF_2H$) | 128~129° C. |
| 77 | Me | Me | H | H | $SO_2CH_2$ | Ph(2,4-$Cl_2$, 3-F, 6-$CF_3$) | 116~118° C. |
| 78 | Me | Me | H | H | $SO_2CH_2$ | Ph(2,3,5-$Cl_3$, 4-OEt) | 118~121° C. |
| 79 | Me | Me | H | H | $SO_2CH_2$ | Ph(2-$CF_3$, 3,4,5-$Cl_3$) | 111~112° C. |
| 80 | Me | Me | H | H | $SO_2CH_2$ | Ph(2,3,4,5,6-$(Me)_5$) | 150~152° C. |
| 81 | Me | Me | H | H | $SO_2CH_2$ | Ph(2-OEt, 3,5-$Cl_2$, 4,6-$(Me)_2$) | 132~134° C. |
| 82 | Me | Me | H | H | $SO_2CH_2$ | Ph(2-Cl, 3-F, 6-OEt) | 101~103° C. |
| 83 | Me | Me | H | H | $SO_2CH_2$ | Ph(2-Cl, 3-F, 6-$OCHF_2$) | 121~123° C. |
| 84 | Me | Me | H | H | $SO_2CH_2$ | Ph(2-F, 3-Cl, 6-CN) | 162~163° C. |

In the formula [I] of the component A, it is preferred that Q is a group $—S(O)_n—(CR^5R^6)_m—$, n is 2, and m is 1;

$R^5$ and $R^6$ are a hydrogen atom;

$R^1$ and $R^2$ are a C1 to C4 alkyl group;

$R^3$ and $R^4$ are a hydrogen atom;

Y is a phenyl group (substituted with same or different, 1 to 5 $R^7$s, and $R_7$ is a hydrogen atom, a C1 to C6 alkyl group (which may be substituted with same or different, 1 to 3 halogen atoms), a C1 to C6 alkoxy group (which may be substituted with same or different, 1 to 3 halogen atoms), a C1 to C6 alkoxycarbonyl group, a C2 to C6 alkinyloxy group, a halogen atom, a nitro group or a cyano group.

Preferred as the herbicide compound of the component B are cyclohexanedione type compounds, uracil type compounds, bipyridium type compounds, thiadiazole type compounds, phenylpyrazole type compounds, isoxazolidinone type compounds, dinitroaniline type compounds, cumyluron, daimuron, methyl-daimuron, flucetosulfuron, triaziflam, pinoxaden. More preferred are profoxydim, tralkoxydim, lenacil, diquat, paraquat, fluthiacet-methyl, pyraflufen-ethyl, clomazone, pendimethalin, cumyluron, daimuron, flucetosulfuron, triaziflam, pinoxaden.

Preferred as the herbicide compounds of the component C are aryloxyphenoxypropionic adic type compounds, sulfonylurea type compounds, imidazolinone type compounds, triazolopyrimidine type compounds, pyrimidinyloxy(thio)benzoic acid type compounds, triazine type compounds, anilide type compounds, oxadiazole type compounds, triazolinone type compounds, oxazolidinedione type compounds, triketone type compounds, pyrazole type compounds, glycine type compounds, phosphinic acid type compounds, pyridine type compounds, phosphoroamidate type compounds, chioroacetamide type compounds, oxyacetamide type compounds, tetrazolinone type compounds, aikaneamide type compounds, thiocarbamate type compounds, benzofuran type compounds, phenoxycarboxylic acid type compounds, benzoic acid type compounds, quinolinecarboxylic acid type compounds, pyraclonil, benzobicyclon, anilofos, cafenstrole, bromobutide, oxaziclomefone, etobenzanid, indanofan, pyributicarb, pyrimisulfan.

More preferred are cyhalofop-butyl, fenoxaprop-P-ethyl, fenoxaprop-ethyl, metamifop, quizalofop-ethyl, quizalofop-P, quizalofop-P-ethyl, quizalofop-P-tefuryl, azimsulfuron, bensulfuron-methyl, halosulfuron-methyl, imazosulfuron, pyrazosulfuron-ethyl, imazamox, imazethapyr, penoxsulam, bispyribac-sodium, pyribenzoxim, pyriftalid, pyriminobac-methyl, pyrithiobac-sodium, dimethametryn, prometryn, simetryn, propanii, bentazone, oxadiargyl, oxadiazon, carfentrazone-ethyl, pentoxazone, mesotrione, tefuryltrion, benzofenap, pyrazolate, glyphosate, glyphosate-trimesium, glufosinate, dithiopyr, butamifos, acetochior, butachlor, dimethenamid, metolachlor, pretilachlor, S-metolachlor, thenylchlor, mefenacet, fentrazamide, naproanilide, esprocarb, molinate, thiobencarb, benfuresate, clomeprop, 2,4-DB, MCPA, MCPB, dicamba, quinclorac, pyraclonil, benzobicyclon, anilofos, cafenstrole, bromobutide, oxaziclomefone, etobenzanid, indanofan, pyributicarb, pyrimisulfan.

In the herbicide composition of the present invention, the contents of the individual components differ dependent upon the relative activities of the individual components but are preferred to be generally as follows.

The content of the component B is 0.001 to 200 parts by weight per 1 part by weight of the component A, preferably 0.005 to 100 parts by weight, more preferably 0.01 to 50 parts by weight.

The content of the component C, when contained, is 0.001 to 200 parts by weight per 1 part by weight of the component A, preferably 0.005 to 100 parts by weight, more preferably 0.01 to 50 parts by weight.

The content of the component D, when contained, is 0.001 to 100 parts by weight per 1 part by weight of the component A, preferably 0.01 to 100 parts by weight, more preferably 0.05 to 30 parts by weight.

The herbicide composition of the present invention may contain, as necessary, other components ordinarily used in agricultural chemicals.

As the other components, there can be mentioned a carrier (e.g. a solid carrier or a liquid carrier), a surfactant, a binder or a tackifier, a thickening agent, a coloring agent, a spreader, a sticker, an anti-icing agent, an anti-caking agent, a collapsing agent, a decomposition inhibitor, etc.

As the other components, there may also be used, as necessary, an antiseptic agent, a plant chip, etc. These other components may be used singly or in combination of two or more kinds.

Explanation is made on the above-mentioned other components.

As the solid carrier, there can be mentioned, for example, natural minerals such as quartz, clay, kaolinite, pyrophyllite, sericite, talc, bentonite, acid clay, attapulgite, zeolite, diatomaceous earth and the like; inorganic salts such as calcium carbonate, ammonium sulfate, sodium sulfate, potassium chloride and the like; organic solid carriers such as synthetic silicic acid, synthetic silicic acid salt, starch, cellulose, plant powder and the like; and plastic carriers such as polyethylene, polypropylene, polyvinylidene chloride and the like. These solid carriers may be used singly or in combination of two or more kinds.

As the liquid carrier, there can be mentioned, for example, alcohols (they are largely divided into monohydric alcohols such as methanol, ethanol, propanol, isopropanol, butanol and the like, and polyhydric alcohols such as ethylene glycol, diethylene glycol, propylene glycol, hexylene glycol, polyethylene glycol, polypropylene glycol, glycerine and the like); polyhydric alcohol derivatives such as propylene type glycol ether and the like; ketones such as acetone, methyl ethyl ketone, methyl isobutyl ketone, diisobutyl ketone, cyclohexanone and the like; ethers such as ethyl ether, dioxane, cellosolve, dipropyl ether, tetrahydrofuran and the like; aliphatic hydrocarbons such as normal paraffin, naphthene, isoparaffin, kerosene, mineral oil and the like; aromatic hydrocarbons such as benzene, toluene, xylene, solvent naphtha, alkylnaphthalene and the like; halogenated hydrocarbons such as dichloroethane, chloroform, carbon tetrachloride and the like; esters such as ethyl acetate, diisopropyl phthalate, dibutyl phthalate, dioctyl phthalate, dimethyl adipate and the like; lactones such as γ-butyrolactone and the like; amides such as dimethylformamide, diethylformamide, dimethyllacetamide, N-alkylpyrrolidinone and the like; nitriles such as acetonitrile and the like; sulfur compounds such as dimethyl sulfoxide and the like; vegetable oils such as soybean oil, rapeseed oil, cotton seed oil, castor oil and the like; and water. These liquid carriers may be used singly or in combination of two or more kinds.

As to the surfactant, there is no particular restriction; however, there is preferred a surfactant which can form a gel or shows a swelling property, in water. There can be mentioned, for example, nonionic surfactants such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkylphenyl ether, polyoxyethylene dialkylphenyl ether, formalin condensate of polyoxyethylene alkylphenyl ether, polyoxyethylene polyoxypropylene block polymer, alkyl polyoxyethylene polypropylene block polymer ether, polyoxyethylene alkylamine, polyoxyethylene fatty acid amide, polyoxyethylene fatty acid bisphenyl ether, polyalkylene benzyl phenyl ether, polyoxyalkylene styryl phenyl ether, acetylenediol, polyoxyalkylene-added acetylenediol, polyoxyethylene ether type silicon, ester type silicon, fluorine-based surfactant, polyoxyethylene castor oil, polyoxyethylene hardened castor oil and the like; anionic surfactants such as salt of alkylsulfate, salt of polyoxyethylene alkyl ether sulfate, salt of polyoxyethylene alkyl phenyl ether sulfate, salt of polyoxyethylene styryl phenyl ether sulfate, salt of alkylbenzenesulfonic acid, salt of ligninsulfonic acid, salt of alkylsulfosuccinic acid, salt of naphthalenesulfonic acid, salt of alkylnaphthalenesulfonic acid, salt of formalin condensate of naphthalenesulfonic acid, salt of formalin condensate of alkylnaphthalenesulfonic acid, fatty acid salt, polycarboxylic acid salt, N-methyl-fatty acid salcosinate, resin acid salt, salt of polyoxyethylene alkyl ether phosphate, salt of polyoxyethylene alkyl phenyl ether phosphate and the like; cationic surfactants, for example, alkylamine salts such as laurylamine hydrochloride, stearylamine hydrochloride, oleylamine hydrochloride, stearylamine acetate, stearylaminopropylamine acetate, alkyltrimethylammonium chloride, alkyldimethylbenzalkonium chloride and the like; and amphoteric surfactants such as amino acid type, betaine type and the like. These surfactants may be used singly or in combination of two or more kinds.

As the binder and the tackifier, there can be mentioned, for example, carboxymethylcellulose or salt thereof, dextrin, water-soluble starch, xanthan gum, guar gum, sucrose, polyvinylpyrrolidone, gum arabi, polyvinyl alcohol, polyvinyl acetate, sodium polyacrylate, polyethylene glycol having an average molecular weight of 6,000 to 20,000, polyethylene oxide having an average molecular weight of 100,000 to 5,000,000, and natural phospholipid (e.g. cephalin acid or lecithin).

As the thickener, there can be mentioned, for example, water-soluble high-molecular compounds such as xanthan gum, guar gum, carboxylmethylcellulose, polyvinylpyrrolidone, carboxyvinyl polymer, acrylic polymer, starch derivative, polysaccharide and the like; and inorganic fine powders such as high-purity bentonite, white carbon and the like.

As the coloring agent, there can be mentioned, for example, inorganic coloring agents such as iron oxide, titanium oxide, Prussian Blue and the like; and organic dyes such as Alizarine dye, azo dye, metallo-phthalocyanine dye and the like.

As the spreader, there can be mentioned, for example, silicon-based surfactant, cellulose powder, dextrin, processed starch, polyaminocarboxylic acid chelate compound, crosslinked polyvinylpyrrolidone, maleic acid and styrene, methacrylic acid copolymer, half ester between polyhydric alcohol polymer and dicarboxylic acid anhydride, and water-soluble salt of polystyrenesulfonic acid.

As the sticker, there can be mentioned, for example, various surfactants such as sodium dialkylsulfosuccinate, polyoxyethylene alkyl ether, polyoxyethylene alkyl phenyl ether, polyoxyethylene fatty acid ester and the like; paraffin; terpene; polyamide resin; polyacrylic acid salt; polyoxyethylene; wax; polyvinyl alkyl ether; alkylphenol formalin condensate; and synthetic resin emulsion.

As the anti-icing agent, there can be mentioned, for example, polyhydric alcohols such as ethylene glycol, diethylene glycol, propylene glycol, glycerine and the like.

As the anti-caking agent, there can be mentioned, for example, polysaccharides such as starch, alginic acid, mannose, galactose and the like; polyvinylpyrrolidone; white carbon; ester gum; and petroleum resin.

As the collapsing agent, there can be mentioned, for example, sodium tripolyphosphate, sodium hexametaphosphate, metal stearate, cellulose powder, dextrin, methacrylic acid ester copolymer, polyvinylpyrrolidone, polyaminocarboxylic acid chelate compound, sulfonated styrene-isobutylene-maleic acid anhydride copolymer, and starch-polyacrylonitrile graft copolymer.

As the decomposition inhibitor, there can be mentioned, for example, desiccants such as zeolite, quick lime, magnesium oxide and the like; anti-oxidants such as phenol type, amine type, sulfur type, phosphoric acid type and the like; and ultraviolet absorbers such as salicylic acid type, benzophenone type and the like.

As the antiseptic agent, there can be mentioned, for example, potassium sorbate, and 1,2-benzothiazolin-3-one.

As the plant chip, there can be mentioned, for example, sawdust, coconut shell, corn rachis, and tobacco stem.

When the herbicide composition of the present invention contains the above-mentioned other components, the contents of the other components are, on weight basis, ordinarily 5 to 95%, preferably 20 to 90% in the case of carrier; ordinarily 0.1 to 30%, preferably 0.5 to 10% in the case of surfactant, and ordinarily 0.1 to 30%, preferably 0.5 to 10% in the case of each of the remaining other components.

The present herbicide composition is used by being made into various formulations such as soluble concentrate, emulsifiable concentrate, wettable powder, dustable powder, oil miscible liquid, water dispersible granule, flowable, suspension, granules, Jumbo formulation, suspoemulsion, and the like. In making such a formulation, there can be mixed at least one kind of agricultural chemical such as other herbicide, microbe for weeding (e.g. *Drechslera monoceras, Xanthomonas campestris* pv. *poae*), insecticide, fungicide, plant growth regulator, fertilizer or the like.

Examples of the fungicide compound which can be mixed or used in combination with the present herbicide composition, are shown below. acibenzolar-S-methyl, azoxystrobin, amisulbrom, aldimorph, isotianil, isoprothiolane, ipconazole, iprodione, iprovalicarb, iprobenfos, imazalil, iminoctadine-albesilate, iminoctadine-triacetate, imibenconazole, edifenphos, ethaboxam, ethoxyquin, etridiazole, epoxiconazole, oxadixyl, oxazinylazole, oxycarboxin, oxine-copper, oxytetracycline, oxpoconazole fumarate, oxolinic acid, octhilinone, ofurace, orysastrobin, o-phenylphenol, kasugamycin, captafol, carpropamid, carbendazim, carboxin, quinoxyfen, chinomethionat, captan, quintozene, guazatine, kresoxim-methyl , chlorothalonil, chloroneb, cyazofamid, diethofencarb, diclocymet, dichlofluanid, diclomezine, dicloran, dithianon, diniconazole, zineb, dinocap, biphenyl, diphenylamine, difenoconazole, difenzoquat, cyflufenamid, diflumetorim, cyproconazole, cyprodinil, simeconazole, dimethomorph, cymoxanil, dimoxystrobin, ziram, silthiofam, streptomycin, spiroxamine, zoxamide, dazomet, tiadinil, thiabendazole, thiophanate-methyl, thifluzamide, thiram, tecnazene, tecloftalam, tetraconazole, debacarb, tebuconazole, dodine, dodemorph, triadimenol, triadimefon, triazoxide, tricyclazole, triticonazole, tridemorph, triflumizole, trifloxystrobin, triforine, tolylfluanid, toiclofos-methyl, tolnifanide, nabam, nitrothal-isopropyl , nuarimol, validamycin, picoxystrobin, bitertanol, piperalin, hymexazol, pyraclostrobin, pyrazophos, pyrifenox, pyributicarb, pyribencarb, pyrimethanil, pyroquilon, vinclozolin, ferbam, famoxadone, fenamidone, fenarimol, fenoxanil, ferimzone, fenbuconazole, fenfuram, fenpropidin, fenpropimorph, fenhexamid, folpet, phthalide, bupirimate, fuberidazole, furametpyr, furalaxyl, fluazinam, fluoxastrobin, fluopicolide, fluoroimide, fluquinconazole, fludioxonii, flusilazole, flusulfamide, flutolanil, flutriafol, flumorph, proquinazid, prochloraz, procymidone, prothioconazole, bronopol, propamocarb-hydrochloride, propiconazole, propineb, probenazole, bromuconazole, hexaconazole, benalaxyl, benalaxyl-M, benomyl, pefurazoate, penconazole, pencycuron, benthiavalicarb-isopropyl, penthiopyrad, boscalid, fosetyl-alminium , polyoxin, polycarbamate, Bordeaux mixture, mancopper, mancozeb, mandipropamid, maneb, myclobutanil, mildiomycin, methasulfocarb, metam, metalaxyl, metalaxyl-M, metconazole, metominostrobin, metrafenone, mepanipyrim, mepronil, 8-hydroxyquinoline sufate, silver compounds, inorganic copper compounds, organic copper compounds, sulfur compounds, organic zinc compounds, potassium hydrogencarbonate, sodium hydrogencarbonate, fatty acid glycerides, *Lentinus edodes* mycelium extract, *Erwinia, pseudomonas, Bacillus, Talaromyces, Trichoderma, Fusarium*.

Also, examples of the insecticide compound which can be mixed or used in combination with the present herbicide composition, are shown below.

1,3-dichloropropene, CL900167, cryolite, DCIP, DNOC, EPN, RU15525, XMC, ZXI8901, acrinathrin, azamethiphos, azinphosethyl, azinphos-methyl, acequinocyl, acetamiprid, acetoprole, acephate, azocyclotin, abamectin, amitraz, alanycarb, aldicarb, alpha-cypermethrin, allethrin, isoxathion, isofenphosmethyl, isocarbophos, isoprocarb, imicyafos, imidacloprid, imiprothrin, indoxacarb, esfenvalerate, ethiofencarb, ethion, ethiprole, etoxazole, etofenprox, ethoprophos, emamectin, endosulfan, empenthrin, oxamyl, oxydemetonmethyl, omethoate, cadusafos, karanjin, cartap, carbaryl, carbosulfan, carbofuran, gamma-cyhalothrin, xylylcarb, quinalphos, kinoprene, chinomethionat, coumaphos, clothianidin, clofentezine, chromafenozide, chlorantranilprole, chlorethoxyfos, chlordane, chloropicrin, chlorpyrifos, chlorpyrifos-methyl, chlorfenapyr, chlorfenvinphos, chlorfluazuron, chlormephos, cyanophos, diafenthiuron, dienochlor, cyenopyrafen, dicrotophos, dichlofenthion, cycloprothrin, dichlorvos, dicofol, dicyclanil, disulfoton, dinotefuran, dinobuton, cyhalothrin, cyphenothrin, cyfluthrin, diflubenzuron, cyflumetofen, diflovidazin, cyhexatin, cypermethrin, dimethylvinphos, dimethoate, silafluofen, cyromazine, spinetoram, spinosad, spirodiclofen, spirotetramat, spiromesifen, sulcofuron-sodium, sulfluramid, sulfotep, zeta-cypermethrin, diazinon, tau-fluvalinate, thiacloprid, thiamethoxam, thiodicarb, thiocyclam, thiosultap, thiofanox, thiometon, tetrachlorvinphos, tetradifon, tetramethrin, tebupirimfos, tebufenozide, tebufenpyrad, tefluthrin, teflubenzuron, demeton-S-methyl, temephos, deltamethrin, terbufos, tralomethrin, transfluthrin, triazamate, triazophos, trichlorfon, triflumuron, trimethacarb, tolfenpyrad, naled, nicotine, nitenpyram, novaluron, noviflumuron, hydroprene, vamidothion, parathion, parathion-methyl, halfenprox, halofenozide, bioallethrin, bioresmethrin, bistrifluoron, hydramethylnon, bifenazate, bifenthrin, pymetrozine, pyraclofos, pyridaphenthion, pyridaben, pyridalyl, pyrifluquinazon, pyriproxyfen, pirimicarb, pyrimidifen, pirimiphos-methyl, famphur, fipronil, fenazaquin, fenamiphos, fenitrothion, fenoxycarb, fenothiocarb, phenothrin, fenobucarb, fenthion, phenthoate, fenvalerate, fenpyroximate, fenbutatin oxide, fenpropathrin, butocarboxim, butoxycarboxim, buprofezin, furathiocarb, prallethrin, fluacrypyrim, flucycloxuron, flucythrinate, flusulfamide, fluvalinate, flupyrazofos, flufenerim, flufenoxuron, flubendiamide, flumethrin, flurimfen, prothiofos, flonicamid, propaphos, propargite, profenofos, propetamphos, propoxur, bromopropylate, beta-cyfluthrin, hexythiazox, hexaflumuron, heptenophos, permethrin, bensultap, benzoximate, bendiocarb, benfuracarb, phoxim, phosalone, fosthiazate, phosphamidon, phosmet, formetanate, phorate, malathion, milbemectin, mecarbam, mesulfenfos, methomyl, metaflumizon, methamidophos, metham, methiocarb, methidathion, methyl isothiocyanate, methoxychlor, methoxyfenozide, methothrin, metofluthrin, methoprene, mevinphos, monocrotophos, lambda-cyhalothrin, rynaxypyr, lufenuron, resmethrin, lepmectin, rotenone.

In using the mixed herbicide composition of the present invention, individual active ingredients may be used directly; or, a composition containing intended active ingredients may be made; or, it is possible to make individual active ingredients into respective formulations and then mix them. In applying the present composition, the individual active ingredients may be applied independently or may be applied simultaneously. Further, the present composition can be used by diluting it with a liquid (e.g. water or a fertilizer), or by adhering it to a carrier (e.g. solid fertilizer, sand or soil), seeds of plant, tubers or the like, or by covering them with the composition. The application can be made to a place where weeds are likely to emerge, or to a plant itself.

The herbicide composition of the present invention exhibits excellent herbicidal effects at a low dosage over a long period from before budding to growing stage, to various weeds which cause problems in, for example, crop lands (e.g. paddy field, upland field and no-tillage field) or non-crop lands (e.g. road, park, artificial slope, garden, and mountain and forest).

The herbicide composition of the present invention exhibits excellent herbicidal effects at a low dosage over a long period from before budding to growing stage, particularly to main weeds growing in transplanted paddy rice cultivation, for example, monocotyledon such as *Echinochloa oryzicola* Vasing, *Echinochloa crus-galli* (L.) P. Beauv. Var. *crus-galli*, *Schoenoplectus juncoides* (Roxb.) Palla, *Schoenoplectus wallichii* (Nees) T.Koyama, *Cyperus flaccidus* R. Br., *Cyperus difformis* L., *Cyperus serotinus* Rottb., *Leptochloa chinensis* Nees., *Fimbristylis miliacea* Vahl and the like, and dicotyledon such as *Monochoria vaginalis* (Burm. f.) Kunth, *Monochoria korsakowii* Regel et Maack, *Lindernia procumbes* (Krock.) Philcox., *vandellia angustifolia* Benth., *Callitriche palustris* L., *Elatine triandra* Schkuhr, *Rotala indica* (Willd.) Kohne var. *uliginosa* (Miq.) Koehne, *Dopatrium juncem* (Roxb.) Buch.-Ham., *Eclipta prostrata* (L.) L. and the like.

Also, the herbicide composition of the present invention can effectively control main weeds growing in upland fields, for example, dicotyledon such as *Fallopia convolvulus* (L.) A. Löve, *Persicaria scabra* (Moench) Mold., *Portulaca oleracea* L., *Chenopodium album* L., *Amaranthus retroflexus* L., *Sinapis arvensis* L., *Sesbania exaltata* Cory, *Senna obtusifolia* (L.) H. S. Irwin & Barneby, *Abutilon theophrasti medicus*, *Sida spinosa* L., *Ipomoea hederacea* Jacq., *Iopomea purpurea* (L.) Roth, *datura stramonium*. L. f. *tatura* (L.) Dabert., *Solanum nigrum* L., *Xanthium strumarium* L., *Helianthus annuus* L., *Convolvulus arvensis* L., *Euphorbia helioscopia* L., *Bidens Frondosa* L., *Ambrosia artemisiifolia* L. and the like, and monocotyledon such as *Echinochloa crus-galli* (L.) P. Beauv. Var. *crus-galli*, *Setaria viridis* (L.) P. Beauv., *Setaria faberi* Herrm., *Setaria glauca* (L.) beauv., *Digitaria ciliaris* (Retz.) Koel., *Eleusine indica* (L.) gaertn., *Sorghum halepense* Pers., *Elytrigia repens* (L.) Desv. Ex Nevski, *Sorghum bicolor* (L.) Moench ssp. *Arundinaceum* (Desv.) de Wet & Harlan and the like.

Further, the herbicide composition of the present invention is highly safe to useful crops and useful plants and can be used to useful crops and useful plants, such as rice, wheat, barley, corn, grain sorghum, soybean, cotton, sugarbeet, oilseed rape, sugarcane, turf glass, tea tree, fruit tree, vegetables, glowers and ornamental plants, trees and the like. Here, the useful crops and useful plants include so-called genetically modified crops which have been trans-formed by genetic engineering and have resistances to herbicides, injurious insects, disease damages, etc., such as corn (e.g. PIONEER 31R87RR), soybean (e.g. ASG ROW SN79624 RR), cotton (e.g. FIBERMAX 960BR), oilseed rape, sugarcane and the like, and plants which show resistances to herbicides, injurious insects, disease damages, etc. owing to breeding and selection.

The present composition is preferably applied as a formulation containing the component A and the component B, or the component A, the component B and the component C, or the component A, the component B and the component D, or the component A, the component B, the component C and the component D, in a total amount of preferably 0.5 to 90% by weight, more preferably 1 to 80% by weight.

The formulation of the present composition can be applied as it is; however, the soluble concentrate, the emulsifiable concentrate, the wettable powder, the dustable powder, the oil miscible liquid, the water dispersible granule, the flowable, the suspension, etc. may be applied by diluting a given amount thereof with water. When the formulation is sprayed in an area of 1 ha (hectare), the amount of the water used for dilution is 10 to 2,000 liters, preferably 100 to 1,000 liters relative to the given amount of the formulation.

The application amount of the present composition varies depending upon the ratio of mixing, the condition of weather, the form of formulation, the timing of application, the method of application, the place of application, the weed to be controlled, and the crop of target. However, the application amount is preferably 1 to 10,000 g, preferably 5 to 4,000 g, more preferably 10 to 1,000 g per 1 ha, in terms of the total amount of the component A and the component B, or the component A, the component B and the component C, or the component A, the component B and the component D, or the component A, the component B, the component C and the component D.

Next, the best mode for carrying out the present invention is described by way of Examples. In the following Examples, parts refer to parts by weight.

EXAMPLES

Formulation Example 1

Granule

The following components were mixed and kneaded sufficiently to obtain a paste-like mixture. The mixture was pushed out from the holes (diameter: 0.7 mm) of a sieve and cut into a length of 0.5 to 1 mm to obtain a granular material. The material was dried in a fluidized dryer to obtain granules.

| | |
|---|---|
| Compound No. 4 | 2 parts |
| Bensulfuron-methyl | 0.5 part |
| Extending agent (1:3 mixture of talc and bentonite) | 80 parts |
| White carbon | 10 parts |
| Mixture of polyoxyethylene sorbitan alkylate, polyoxyethylene alkylaryl polymer and alkylaryl sulfonate | 7.5 parts |
| Water | 10 parts |

Formulation Example 2

Wettable Powder

The following components were mixed and kneaded to obtain a wettable powder.

| | |
|---|---|
| Compound No. 1 | 2 parts |
| Bensulfuron-methyl | 0.5 part |
| Polyoxyethylene octyl phenyl ether | 0.5 part |
| Sodium salt of β-naphthalenesulfonic acid-formalin condensate | 0.5 part |
| Diatomaceous earth | 26.5 parts |
| Clay | 70 parts |

Formulation Example 3

Wettable Powder

The following components were mixed and kneaded to obtain a wettable powder.

| | |
|---|---|
| Compound No. 54 | 2 parts |
| Clomazone | 5 parts |
| Fenclorim | 2 parts |
| Polyoxyethylene octyl phenyl ether | 0.5 part |
| Sodium salt of β-naphthalenesulfonic acid-formalin condensate | 0.5 part |
| Diatomaceous earth | 20 parts |
| Clay | 70 parts |

Formulation Example 4

Wettable Powder

The following components were mixed and kneaded to obtain a wettable powder.

| | |
|---|---|
| Compound No. 31 | 2 parts |
| Bensulfuron-methyl | 0.1 part |
| Daimuron | 7.5 parts |
| Polyoxyethylene octyl phenyl ether | 0.5 part |
| Sodium salt of β-naphthalenesulfonic acid-formalin condensate | 0.5 part |
| Diatomaceous earth | 20 parts |
| Clay | 69.4 parts |

Formulation Example 5

Wettable Powder

The following components were mixed and kneaded to obtain a wettable powder.

| | |
|---|---|
| Compound No. 33 | 2 parts |
| Clomazone | 5 parts |
| Pyrazosulfuron-ethyl | 0.3 part |
| Polyoxyethylene octyl phenyl ether | 0.5 part |
| Sodium salt of β-naphthalenesulfonic acid-formalin condensate | 0.5 part |
| Diatomaceous earth | 20 parts |
| Clay | 71.7 parts |

Formulation Example 6

Wettable Powder

The following components were mixed and kneaded to obtain a wettable powder.

| | |
|---|---|
| Compound No. 34 | 2 parts |
| Clomazone | 5 parts |
| Pyrazosulfuron-ethyl | 0.3 part |
| Fenclorim | 2 parts |
| Polyoxyethylene octyl phenyl ether | 0.5 part |

-continued

| | |
|---|---|
| Sodium salt of β-naphthalenesulfonic acid-formalin condensate | 0.5 part |
| Diatomaceous earth | 18.7 parts |
| Clay | 71 parts |

Next, the effect of the herbicide composition of the present invention is described by way of Test Examples.

Test Example 1

Test for herbicidal effect by paddy soil treatment

A paddy soil was filled in a plastic pot of 100 cm² and subjected to puddling. Thereinto were sowed seeds of *Echinochloa oryzicola* Vasing, *Monochoria vaginalis* (Burm. f.) Kunth, *Schoenoplectus juncoides* (Roxb.) Paila or *Cyperus serotinus* Rottb., after which water was filled at a depth of 3 cm. Each pot was placed in a greenhouse for raising, At a timing when the *Echinochloa oryzicola* Vasing reached about a two-leaf stage, a seedling of two-leaf stage rice (variety: *Kinnanpuu*) was transplanted into each pot at a depth of 2 cm. A wettable powder prepared in accordance with Formulation Example 2 was diluted with water based on the total sum of the active ingredients, and the dilution was dropped on the water surface of the pot. Then, the pot was allowed to stand for raising. The herbicidal effect of the wettable powder was examined at the 28th day of the treatment (the dropping of the dilution) in accordance with the standard of Table 4. The results are shown in Table 5.

TABLE 4

| Index | Herbicidal effect (extent of growth inhibition) and phytotoxicity |
|---|---|
| 10 | Herbicidal effect (growth inhibition) or phytotoxicity of 100% |
| 9 | Herbicidal effect or phytotoxicity of 90% to less than 100% |
| 8 | Herbicidal effect or phytotoxicity of 80% to less than 90% |
| 7 | Herbicidal effect or phytotoxicity of 70% to less than 80% |
| 6 | Herbicidal effect or phytotoxicity of 60% to less than 70% |
| 5 | Herbicidal effect or phytotoxicity of 50% to less than 60% |
| 4 | Herbicidal effect or phytotoxicity of 40% to less than 50% |
| 3 | Herbicidal effect or phytotoxicity of 30% to less than 40% |
| 2 | Herbicidal effect or phytotoxicity of 20% to less than 30% |
| 1 | Herbicidal effect or phytotoxicity of 10% to less than 20% |
| 0 | Herbicidal effect (growth inhibition) or phytotoxicity of less that 10% |

TABLE 5

| Components | Dose (g a.i./10a) | Transplanted Rice | *Echinochloa oryzicola* | *Monochoria vaginalis* | *Schoenoplectus juncoides* | *Cyperus serotinus* |
|---|---|---|---|---|---|---|
| Compound 1 | 20 | 1 | 8 | 4 | 6 | 2 |
| Clomazone | 80 | 0 | 2 | 7 | 5 | 5 |
| Bensulfuron-methyl | 1 | 0 | 3 | 8 | 7 | 7 |
| Compound 1 + Clomazone | 20 + 80 | 1 | 10 | 10 | 9 | 8 |
| Compound 1 + Clomazone + Bensulfuron-methyl | 20 + 80 + 1 | 1 | 10 | 10 | 10 | 10 |
| Compound 1 | 20 | 1 | 8 | 4 | 6 | 2 |
| Daimuron | 150 | 0 | 0 | 2 | 7 | 3 |
| Bensulfuron-methyl | 1 | 0 | 3 | 8 | 7 | 7 |
| Compound 1 + Daimuron | 20 + 150 | 0 | 9 | 8 | 10 | 8 |
| Compound 1 + Daimuron + Bensulfuron-methyl | 20 + 150 + 1 | 0 | 10 | 10 | 10 | 10 |
| Compound 31 | 20 | 1 | 8 | 5 | 4 | 2 |
| Daimuron | 150 | 0 | 0 | 2 | 7 | 3 |
| Pyrimisulfan | 1 | 1 | 6 | 6 | 9 | 9 |
| Compound 31 + Daimuron | 20 + 150 | 0 | 9 | 9 | 10 | 8 |
| Compound 31 + Daimuron + Pyrimisulfan | 20 + 150 + 1 | 0 | 10 | 10 | 10 | 10 |
| Compound 54 | 20 | 1 | 8 | 5 | 2 | 1 |
| Daimuron | 150 | 0 | 0 | 2 | 7 | 3 |
| Bensulfuron-methyl | 1 | 0 | 3 | 8 | 7 | 7 |
| Compound 54 + Daimuron | 20 + 150 | 0 | 9 | 8 | 8 | 8 |
| Compound 54 + Daimuron + Bensulfuron-methyl | 20 + 150 + 1 | 0 | 10 | 10 | 10 | 10 |

Test Example 2

Test for Herbicidal Effect by Paddy Foliage Treatment

A paddy soil was filled in a plastic pot of 100 cm² and subjected to puddling. Thereinto were sowed seeds of rice (variety: *Akebono*), *Echinochloa crusgalli* (L.) P. Beauv. Var. *crus-galli*, *Leptochloa chinensis* Nees., *Monochoria vaginalis* (Burm. f.) Kunth, or *Fimbristylis miliacea* Vahl, after which each plant was raised in a greenhouse in a drained treatment until the *Echinochloa crus-galli* (L.) P. Beauv. Var. *crus-galli* reached a two-leaf stage. At that timing, a wettable powder prepared in accordance with Formulation Example 2 was diluted with water based on the total sum of the active ingredients, and the dilution was sprayed at a rate of 20 liters/10 ares using a micro-sprayer (a product of OLYMPOS). 3 days after the spraying, water was filled at a depth of 3 cm. Then, the pot was allowed to stand for raising. The herbicidal effect of the wettable powder was examined at the 28th day of the treatment (the spraying of the dilution) in accordance with the standard of Table 4. The results are shown in Table 6.

TABLE 6

| Components | Dose (g a.i./10a) | Direct seeding rice | *Echinochloa crus-galli* | *Leptochloa chinensis* | *Monochoria vaginalis* | *Fimbristylis miliacea* |
|---|---|---|---|---|---|---|
| Compound 33 | 20 | 1 | 7 | 6 | 6 | 3 |
| Clomazone | 50 | 1 | 2 | 2 | 7 | 3 |
| Pyrazosulfuron-ethyl | 3 | 1 | 2 | 0 | 6 | 8 |
| Compound 33 + Clomazone | 20 + 50 | 1 | 10 | 9 | 10 | 8 |
| Compound 33 + Clomazone + Pyrazosulfuron-ethyl | 20 + 50 + 3 | 1 | 10 | 9 | 10 | 10 |
| Compound 34 | 20 | 2 | 5 | 3 | 5 | 4 |
| Clomazone | 50 | 1 | 2 | 2 | 7 | 3 |
| Pyrazosulfuron-ethyl | 3 | 1 | 2 | 0 | 6 | 8 |
| Compound 34 + Clomazone | 20 + 50 | 2 | 9 | 9 | 10 | 8 |
| Compound 34 + Clomazone + Pyrazosulfuron-ethyl | 20 + 50 + 3 | 2 | 9 | 9 | 10 | 10 |
| Compound 34 + Clomazone + Pyrazosulfuron-ethyl + Fenclorim | 20 + 50 + 3 + 20 | 0 | 9 | 9 | 10 | 10 |
| Compound 31 | 20 | 2 | 6 | 3 | 3 | 2 |
| Pendimethalin | 80 | 1 | 5 | 5 | 2 | 3 |
| Pyrazosulfuron-ethyl | 3 | 1 | 2 | 0 | 6 | 8 |
| Compound 31 + Pendimethalin | 20 + 80 | 2 | 10 | 10 | 6 | 6 |
| Compound 31 + Pendimethalin + Pyrazosulfuron-ethyl | 20 + 80 + 3 | 2 | 10 | 10 | 10 | 10 |
| Compound 31 + Pendimethalin + Pyrazosulfuron-ethyl + Fenclorim | 20 + 80 + 3 + 20 | 0 | 10 | 10 | 10 | 10 |
| Compound 54 | 20 | 2 | 7 | 6 | 4 | 2 |
| Clomazone | 50 | 1 | 2 | 2 | 8 | 6 |
| Compound 54 + Clomazone | 20 + 50 | 2 | 10 | 10 | 10 | 9 |
| Compound 54 + Clomazone + Fenclorim | 20 + 50 + 20 | 0 | 10 | 10 | 10 | 9 |

The invention claimed is:

1. A herbicide composition comprising, as active ingredients, a component A which is at least one compound selected from the group consisting of isoxazoline derivatives of formula [I], as described below and salts thereof, and a component B as described below and salts thereof, wherein component A is at least one compound of the following formula I:

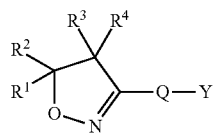

[I]

wherein:
Q is a group —S(O)$_n$—(CR$^5$R$^6$)$_m$—; n is an integer of 0 or 2; m is 1; and R$^5$ and R$^6$ are each a hydrogen atom;
R$^1$ and R$^2$ are each a C1 to C8 alkyl group;
R$^3$ and R$^4$ are each a hydrogen atom; and
Y is a phenyl group, substituted with same or different, 1 to 5 R$^7$s, wherein R$^7$ is:
  a hydrogen atom,
  a C1 to C6 alkoxy group, which may be substituted with same or different 1 to 3 halogen atoms,
  a C2 to C6 alkinyloxy group, or
  a halogen atom,
and wherein Component B is at least one compound selected from the group consisting of clomazone, and daimuron.

2. A herbicide composition according to claim 1, wherein: in the group —S(O)$_n$(CR$^5$R$^6$)$_m$—, n is 2.

3. A herbicide composition containing, as active ingredients, a herbicide composition set forth in claim 2 and a component C selected from the group consisting of aryloxyphenoxypropionic acids, bensulfuronmethyl, pyrazosulfuron-ethyl, pyrimisulfan, and salts thereof.

4. A herbicide composition containing, as active ingredients, a herbicide composition set forth in claim 2 and a component D selected from the group consisting of fenclorim, and salts thereof.

5. A herbicide composition containing, as active ingredients, a herbicide composition as set forth in claim 3 and a component D selected from the group consisting of fenclorim, and salts thereof.

6. A herbicide composition according to claim 2, which contains the component A and the component B at a weight ratio of 1:0.001 to 1: 200.

7. A herbicide composition according to claim 3, which contains the component A, the component B and the component C at a weight ratio of 1:0.001: 0.001 to 1:200:200.

8. A herbicide composition according to claim 4, which contains the component A, the component B and the component D at a weight ratio of 1:0.001: 0.001 to 1:200:100.

9. A herbicide composition according to claim 5, which contains the component A, the component B, the component C and the component D at a weight ratio of 1:0.001:0.001: 0.001 to 1:200:200:100.

10. A herbicide composition containing a herbicide composition set forth in claim 1, in an amount showing a herbicidal activity, and at least one additional component selected from the group consisting of inactive liquid carriers, solid carriers and surfactants.

11. A method for preparing a herbicide composition set forth in claim 5, which comprises mixing a component A, a component B, a component C, a component D, and at least one additional component selected from the group consisting of inactive liquid carriers, solid carriers, and surfactants.

12. A method for controlling undesired vegetation, which comprises applying the active ingredients contained in a herbicide composition as set forth in claim 1, at one time or in portions, to undesired vegetation.

13. A herbicide composition according to claim 3, which contains the component A, the component B and the component C at a weight ratio of 1:1: 0.001 to 1:200:1.

* * * * *